United States Patent
Papac

(10) Patent No.: US 10,426,339 B2
(45) Date of Patent: Oct. 1, 2019

(54) APPARATUSES AND METHODS FOR PARAMETER ADJUSTMENT IN SURGICAL PROCEDURES

(71) Applicant: Novartis AG, Basel (CH)

(72) Inventor: Michael James Papac, North Tustin, CA (US)

(73) Assignee: Novartis AG (CH)

( * ) Notice: Subject to any disclaimer, the term of this patent is extended or adjusted under 35 U.S.C. 154(b) by 275 days.

(21) Appl. No.: 14/994,807

(22) Filed: Jan. 13, 2016

(65) Prior Publication Data

US 2017/0196453 A1   Jul. 13, 2017

(51) Int. Cl.
| | |
|---|---|
| *A61B 3/00* | (2006.01) |
| *A61B 3/13* | (2006.01) |
| *A61B 3/10* | (2006.01) |
| *G02B 21/00* | (2006.01) |
| *G02B 21/36* | (2006.01) |
| *G06F 3/041* | (2006.01) |
| *G06F 3/0484* | (2013.01) |
| *A61F 9/007* | (2006.01) |
| *A61F 9/008* | (2006.01) |
| *A61B 34/00* | (2016.01) |
| *A61B 90/20* | (2016.01) |
| *A61B 90/30* | (2016.01) |

(52) U.S. Cl.
CPC ............... *A61B 3/13* (2013.01); *A61B 3/10* (2013.01); *A61B 3/102* (2013.01); *A61F 9/008* (2013.01); *A61F 9/00736* (2013.01); *G02B 21/0012* (2013.01); *G02B 21/368* (2013.01); *G06F 3/0416* (2013.01); *G06F 3/04847* (2013.01); *A61B 34/25* (2016.02); *A61B 90/20* (2016.02); *A61B 2090/306* (2016.02)

(58) Field of Classification Search
CPC .......... G01J 9/00; G01J 1/0414; G01J 1/0437; G01J 2003/064; A61B 3/10; A61B 3/0025; A61B 3/132; A61B 3/14; A61B 3/152; A61B 3/1015; A61B 3/102; A61B 3/1035; A61B 3/112; A61B 3/113; A61B 3/11; A61F 2009/00848

See application file for complete search history.

(56) References Cited

U.S. PATENT DOCUMENTS

| | | | |
|---|---|---|---|
| 9,585,553 B2* | 3/2017 | Zhou | A61B 3/1015 |
| 2010/0145320 A1 | 6/2010 | Horvath et al. | |
| 2011/0257638 A1 | 10/2011 | Boukhny et al. | |
| 2014/0055749 A1* | 2/2014 | Zhou | A61B 3/0025 |
| | | | 351/214 |

(Continued)

FOREIGN PATENT DOCUMENTS

WO    2005122979 A2   12/2005

*Primary Examiner* — Frank F Huang
(74) *Attorney, Agent, or Firm* — Keiko Ichiye, Esq.

(57) ABSTRACT

Systems, apparatuses, and methods of and for an ophthalmic surgical system are disclosed. An ophthalmic surgical system may include a surgical microscope through which a user may view a surgical site. A display device in communication with the surgical microscope may output a graphical overlay into the field of view of the surgical microscope. The graphical overlay may display one or more configurable parameters associated with a surgical tool. A user may adjust the one or more configurable parameters with an input device while visualizing the field of view.

20 Claims, 5 Drawing Sheets

(56) References Cited

U.S. PATENT DOCUMENTS

2014/0063455 A1* 3/2014 Zhou .................... A61B 3/1015
351/206
2014/0171959 A1    6/2014 Yacono
2017/0156588 A1* 6/2017 Ren ........................ A61B 34/20

* cited by examiner

APPARATUSES AND METHODS FOR PARAMETER ADJUSTMENT IN SURGICAL PROCEDURES

TECHNICAL FIELD

The present disclosure is directed to ophthalmic surgical devices, systems, and methods. More particularly, but not by way of limitation, the present disclosure is directed to devices, systems, and methods of inputting selectable operational parameters of an ophthalmic surgical system while viewing the surgical field through a surgical microscope.

BACKGROUND

During a surgical procedure, a surgical microscope is used to view a surgical field, such as the patient's eye. A surgical console for use in a surgical procedure includes various systems used to perform the surgical procedure. For example, the surgical console may have a light source to illuminate the surgical field, a drive system to operate a surgical probe, a fluidics subsystem to control intraocular pressure, among other features. Various tools, such as an illuminator, a vitrectomy probe, and an infusion cannula, are connected to the surgical console. These tools may be inserted into a patient's eye by a user, such as a surgeon or other medical professional, during the surgical procedure. The user may perform the surgical procedure by manipulating one or more of the tools while viewing the surgical field through the surgical microscope.

Typically, the tools' operating settings are controlled on the surgical console itself. The operating settings for different tools may include a desired intraocular pressure, a desired cut speed, and a desired illumination level, among others. In some instances, dials or knobs on the console are used to change these settings. In other instances, a touch screen display is integrated in the surgical console. The user may interact with a graphical user interface (GUI) of the console display to make changes.

Changing a console setting during a procedure disrupts the procedure. For example, the user may need to look up from the microscope optics, move to the console, and manually change the setting on the console. Alternatively, the user may call out what changes he or she wants made to an assistant who must then move to the console to manually change the setting. Such procedures to change console settings introduce inefficiencies into the surgical workflow. Rather than maintaining focus on the surgical field, the user's attention and/or body are diverted to the surgical console or an assistant is required solely to respond to the user.

SUMMARY

The present disclosure describes example ophthalmic surgical systems that may include a surgical microscope operable to provide a field of view of a surgical site to a user. The system may also include a display device in communication with the surgical microscope. The display device may be operable to output a graphical overlay into the field of view of the surgical microscope. The system may also include a tool operable to perform a surgical task associated with the surgical site while the user visualizes the field of view using the surgical microscope. The graphical overlay may display one or more configurable parameters associated with the tool. The system may also include an input device operable to adjust the one or more configurable parameters associated with the tool using the graphical overlay while the user visualizes the field of view using the surgical microscope.

The present disclosure also discloses ophthalmic surgical systems that include computing devices operable to output display data representative of a graphical overlay. The data representative of the graphical overplay may include one or more configurable parameters associated with a tool operable to perform a surgical task during an ophthalmic surgical procedure. The computing devices may also be operable to receive a user input using the graphical overlay. The user input may adjust the one or more configurable parameters associated with the tool. The computing devices may also be operable to output, to the tool, a control signal based on the user input. The control signal may adjust the one or more configurable parameters associated with the tool. The computing devices may also include a display device operable to provide the graphical overlay into a field of view of a surgical microscope.

In addition, the present disclosure is directed to methods of operating an ophthalmic surgical system. The methods may include outputting, from a computing device to a display device, display data representative of a graphical overlay. The graphical overlay may include one or more configurable parameters associated with a tool operable to perform a surgical task during an ophthalmic surgical procedure. The methods also may include displaying the graphical overlay within a field of view of a surgical microscope operable by a user to visualize a patient eye. The methods may include receiving a user input, using the graphical overlay, that may adjust the one or more configurable parameters associated with the tool. Some methods may also include outputting, to the tool, a control signal based on the user input. The control signal may adjust the one or more configurable parameters associated with the tool.

The various aspects of the disclosure may include one or more of the following features. The display device may be operable to simultaneously display the graphical overlay and the field of view of the surgical site. The graphical overlay may include a graphical representation of at least one of a set point or a current status of the one or more configurable parameters. The graphical overlay may include an adjustment field operable to modify the one or more configurable parameters. The tool may include at least one of a cutting probe, a vitrectomy probe, a phacoemulsification probe, a laser probe, an ablation probe, a diathermy probe, a vacuum probe, a flushing probe, scissors, forceps, an infusion device, an aspiration device, an illumination device, a laser, or an endoscopic visualization probe. The one or more parameters may include at least one of a cut speed, an operating frequency, an infusion pressure, an alternative infusion pressure, an illumination level, an illumination wavelength, a vacuum aspiration level, a laser power, a laser pulse duration, a laser wavelength, laser energy diathermy power, or diathermy energy. The input device may include at least one of an imaging device, a footswitch, a touch-sensitive pad, a tablet device, a gesture control device, a voice recognition device, or a gaze control device. The system may further include a surgical console in communication with at least one of the surgical microscope, the display device, the tool, or the input device. The surgical console may be configured to receive and respond to control signals indicative of adjustment of the one or more configurable parameters. The system may further comprise a second tool operable to perform a surgical task associated with the surgical site while the user visualizes the field of view using the surgical microscope. The graphical overlay may display one or more configurable parameters associated with the second tool. The user input may be representative of at least one of a user gesture, a tool motion, a selection of a footswitch button, or a selection of a tool button. The computing device may be operable to receive, from the input device, a user input to selectively show or hide the graphical overlay.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate implementations of the systems, devices, and methods disclosed herein and together with the description, serve to explain the principles of the present disclosure.

Figure 1:
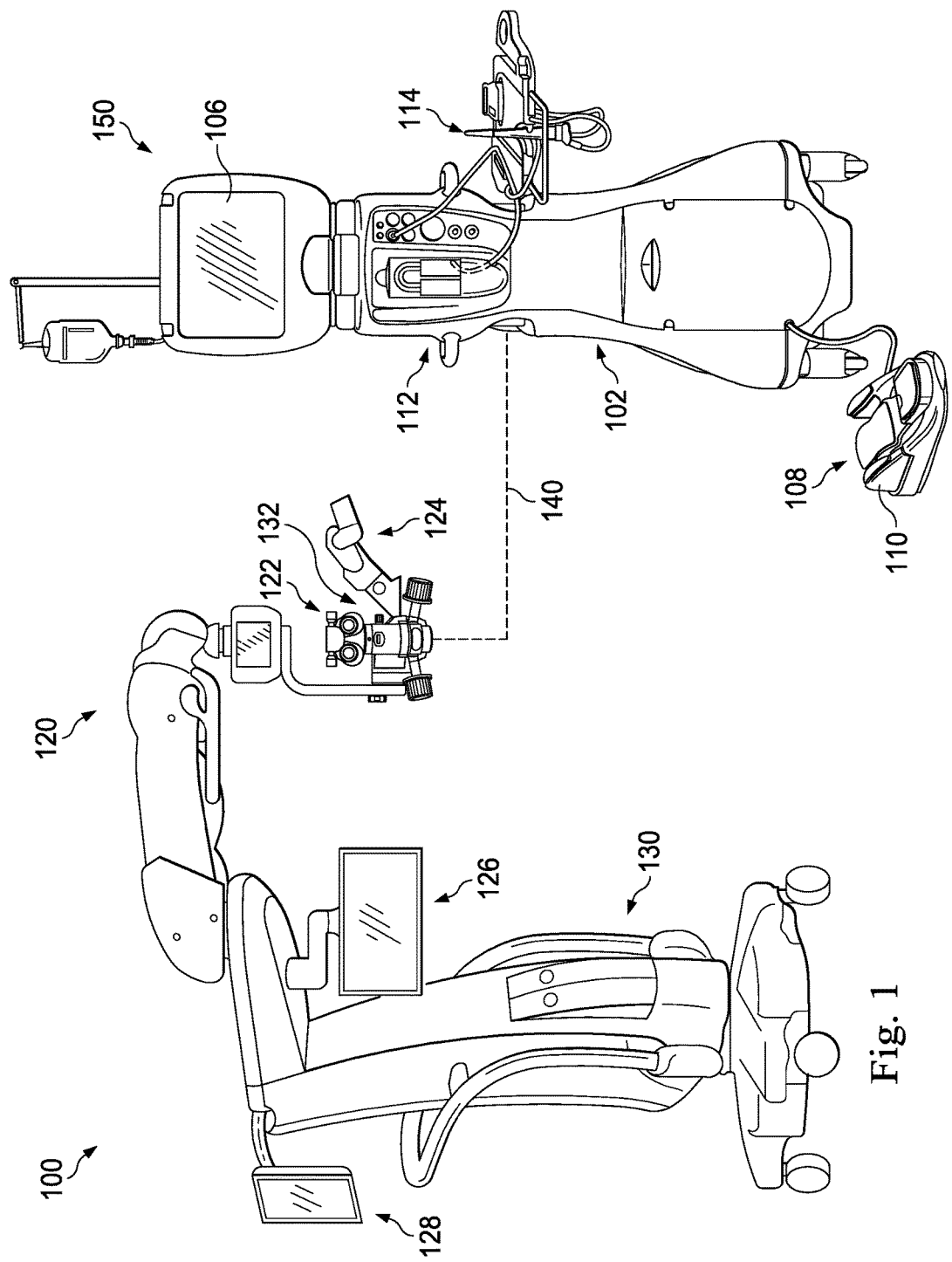
FIG. 1 is an illustration of an example ophthalmic surgical system.

These figures will be better understood by reference to the following detailed description.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

The present disclosure relates generally to devices, systems, and methods for adjusting ophthalmic surgical console settings via a heads up display on a surgical microscope. A graphical overlay may be provided into the optical path of the surgical microscope allowing the user to simultaneously view the surgical field and the graphical overlay. The graphical overlay provides a GUI including console settings associate with various surgical tool(s). The user may provide user input to select the console settings via the GUI. For example, the user input may be received via a footswitch, tool tracking system, gesture/motion recognition system, or other input mechanism or device.

The devices, systems, and methods of the present disclosure provide numerous advantages. The efficiency of surgical procedures may be improved by eliminating extra steps a user would have to take during a surgical procedure to change a console setting. For example, a surgeon may directly change the console setting without relying on an assistant or moving away from the surgical microscope. The safety of surgical procedures may also be improved by allowing the user to maintain focus on the surgical field. Because the graphical overlay is viewable through the surgical microscope, the user may maintain his or her focus on the field of view of the surgical microscope.

FIG. 1 illustrates an example ophthalmic surgical system 100. The system 100 includes a surgical microscope 120 in communication with a surgical console 150 along a representative communication path 140. The system 100 may be used in various ophthalmic procedures, such as an anterior segment procedure, a posterior segment procedure, a vitreoretinal procedure, a vitrectomy procedure, a cataract procedure, and/or other desired procedures.

In the example implementation shown, the surgical microscope 120 includes eyepieces 122, 124, a support or frame 130, and an optical train housing 132. A patient's eye may be viewed using the surgical microscope 120 when light reflected from the eye travels through the optical train housing 132 and is received at the eyepieces 122, 124. The user's view of the surgical site or surgical field through the eyepieces 122, 124 may be referenced as the heads up display of the surgical microscope 120. In some instances, one of the eyepieces 122, 124 functions as the primary eyepiece used by a primary user, such as a surgeon or other medical professional. The other of the eyepiece 122, 124 may function as a secondary eyepiece used by a secondary user, such as an assistant or other medical professional. The optical train housing 132 includes one or more optical components, includes lenses, mirrors, filters, gratings, and/or other elements, that allow the user to view the surgical field. The optical train housing 132 may also include optical components for directing the light reflected from the patient eye into separate optical pathways for each of the eyepieces 122, 124. The microscope 120 discussed herein may be a monocular or binocular microscope, and may be a compound, stereo, or digital microscope.

The surgical microscope 120 may also include display devices or screens 126, 128. The display devices may be fixedly or removably coupled to the surgical microscope 120. In some implementations, the display devices 126, 128 display a real-time video feed of the surgical field as observed by the user via the eyepieces 122, 124. As described with reference to FIG. 2, below, the surgical microscope 120 may include an imaging device to capture the user's field of view. In other instances, the display devices 126, 128 may output a graphical representation of console settings and/or medical information related to the patient eye. In some instances, the graphical representation of information related to the patient eye may include an optical coherence tomography (OCT) image, a fluorescein angiography image, an indocyanine green angiography image, a fundus photography image, a slitlamp biomicroscopy image, other suitable images, and/or combinations thereof.

The surgical console 150 includes a base housing 102 and one or more subsystems that may be used during the ophthalmic surgical procedure. The subsystems may include associated tools inserted into the eye by the user to perform surgical tasks. For example, one of the subsystems may be a surgical instrument control system 112 in communication with a hand-held surgical instrument 114. The surgical instrument 114 may be coupled to the console 150 via a conduit such that the instrument 114 and the console 150 are in mechanical, electrical, pneumatic, and/or other desired type of communication. The surgical instrument 114 may be a cutting probe, a vitrectomy probe, a phacoemulsification probe, a laser probe, an ablation probe, a vacuum probe, a flushing probe, scissors, forceps, an endoscopic visualization probe, other ophthalmic devices, and/or combinations thereof. In some implementations, the endoscopic visualization probe can facilitate direct visualization and/or visualization of the surgical field using optical coherence tomography (OCT). A foot pedal subsystem 108 of the console 150 includes a foot pedal 110 having a number of foot-actuated controls. For example, the user may depress the foot pedal 110 to varying degrees during the surgical procedure to increase and decrease the operating frequency of a surgical instrument, such as, for example, surgical instrument 114. Other subsystems and/or associated surgical tools of the console 150 are described below with reference to FIG. 2.

The console 150 also includes a display device or screen 106. The user may control the various parameters associated with the tool(s) and/or subsystem(s) of the console 150 using the display device 106. For example and without limitation, when the display device 106 is touch-sensitive, the infusion pressure may be set or changed via a touch input. According to aspects of the present disclosure, various console parameters may be controlled via a graphical user interface (GUI) overlaid onto the user's field of view through the surgical microscope 120. The communication path 140 enables the surgical microscope 120 to communicate with the console 150 to control the various console parameters in a manner described in greater detail below.

Figure 2:
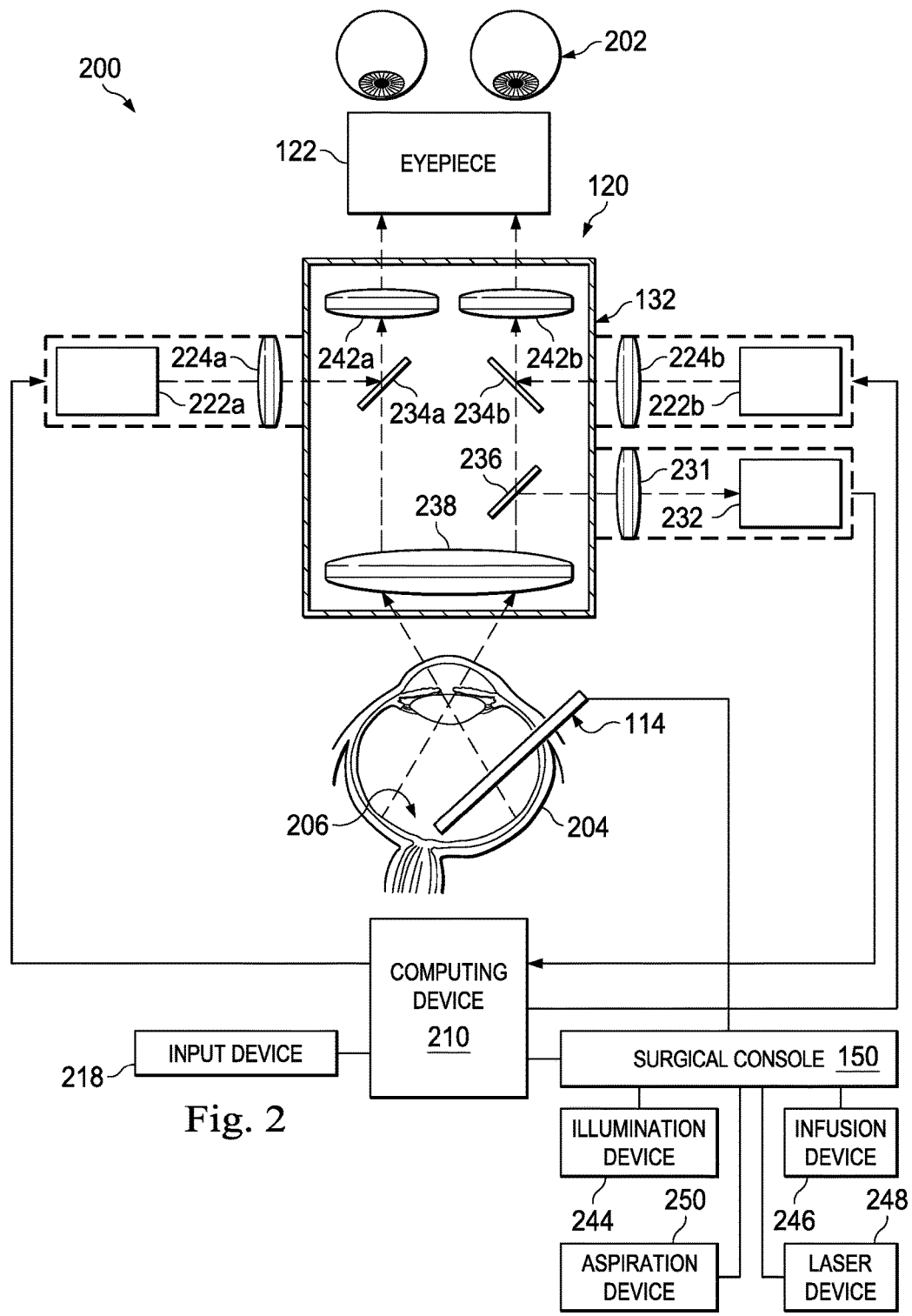
FIG. 2 is a block diagram of an example ophthalmic surgical system.

FIG. 2 illustrates an ophthalmic surgical system 200 according to another implementation of the present disclosure. The system 200 is similar in many respects to the system 100 of FIG. 1 and much of the description above equally applies to the system 200. In that regard, the system 200 includes the surgical microscope 120 and the surgical console 150. A user 202 observes a surgical field 206 of an eye 204 by looking through the eyepiece 122 of the surgical microscope 120. The surgical field 206 may include various biological tissues in the eye, including the vitreous humor, transparent membranes, portions of the retina, blood vessels, and/or other portions of the eye. The user 202 performs the surgical procedure using one or more tools, such as the surgical instrument 114 shown positioned within the surgical field 206. In a vitrectomy procedure, for example, the surgical instrument 114 may be inserted into the vitreous chamber via an incision through the sclera in the pars plana.

In addition to the surgical instrument 114, various other tool(s) may be positioned within or used to treat the surgical field 206 while the user performs the surgical procedure. For example, the surgical console 150 may be in communication with an illumination device 244, an infusion device 246, a laser device 248, and/or an aspiration device 250. In some implementations, the illumination device 244 is an ophthalmic chandelier, spot illuminator, endo-illuminator, fiber optic light source, and/or other device that illuminates the surgical field 206. In some implementations, the infusion device 246 is an infusion cannula that delivers fluid into the eye 204, such as to maintain intraocular pressure and/or flush material from the eye 204. In some implementations, the laser device 248 delivers laser light to the eye 204, such as, for example, to create incisions, cauterize blood vessels during photocoagulation, and/or other surgical procedures using laser energy. In some implementations, the aspiration device 250 may include a lumen for evacuating fluid and/or biological material from the surgical field 206. The illumination device 244, the infusion device 246, the laser device 248, and/or the aspiration device 250 may be coupled to the console 150 via a conduit such that the tool and the console 150 are in mechanical, electrical, pneumatic, fluid, and/other desired type of communication. One or more of the tools may be integrated into a single hand-held instrument. For example, an aspiration lumen may be integrated into the surgical instrument 114 such that the aspiration device 250 and the surgical instrument 114 are a single hand-held instrument. The surgical instrument 114, the illumination device 244, the infusion device 246, the laser device 248, and/or the aspiration device 250 each have one or more adjustable operating parameters. Collectively, the operating parameters may be referenced as console settings. In one aspect of the present disclosure, the user 202 may set and/or adjust the operating parameters via a GUI displayed in the optical path of the surgical microscope.

Although several devices, e.g., the illumination device 244, the infusion device 246, the laser device 248, and the aspiration device 250, are described, the scope of the disclosure is not so limited. Rather, other types of devices for use in the course of a surgical procedure are also within the scope of the present disclosure.

The system 200 also includes a computing device 210 coupled to the surgical microscope 120 and the surgical console 150. In some implementations, the computing device 210 is distinct from the surgical microscope 120 and/or the surgical console 150. In other implementations, the computing device 210 is integrated into the surgical microscope 120 and/or the surgical console 150. An implementation of the computing device 210 is described in greater detail further below with reference to FIG. 3. Generally, the computing device 210 includes processing and memory components operable to execute computer instructions related to control of various surgical tools. For example, the computing device 210 may transmit control signals to the surgical instrument 114, the illumination device 244, the infusion device 246, the laser device 248, and/or the aspiration device 250. The computing device 210 may generate the control signals in response to one or more user inputs to increase, decrease, and/or otherwise modify the operating parameters of one or more tools. As described herein, the user input may be received via a GUI overlaid onto the user's field of view through the surgical microscope 120. As described further below with reference to FIG. 3, the display data associated with the GUI may be generated by the computing device 210.

The system 200 includes an input device 218 in communication with the computing device 210. The user may provide user input to set and/or change console settings via the input device 218. In particular, the input device 218 may be used to make selections within the GUI that is overlaid onto the user's field of view. The user input device 218 may be distinct from or integrated with the surgical microscope 120, the console 150, the surgical instrument 114, the illumination device 244, the infusion device 246, the laser device 248, and/or the aspiration device 250. In some implementations, the user input device 218 is a remote device, a wireless mouse, or a touchscreen display that controls a selection cursor within the GUI. In some implementations, the user input device 218 is the foot pedal 108, as illustrated in the example shown in FIG. 1. In that regard, user input device 218 may include button(s), switch(es), a scroll device, a joystick, and/other controls that allow a user to provide different types of inputs, including control of a cursor within the GUI. In some instances, each of the individual controls of the user input device 218 may be mapped to specific commands to facilitate efficient selection and/or adjustment of console settings.

In some implementations, the input device 218 includes a gesture or movement recognition system or device. The gesture or movement recognition system may include an imaging device that tracks the user's hands or fingers, for example. The imaging data acquired by the imaging device may be processed by the computing device 210 to recognize various user inputs. The user may make gestures or movements with his or her fingers or hands while maintaining grip on the hand-held tools that are disposed within the surgical field 206. In that regard, the input device 218 can be a control device using a gesture as an input. In other implementations, one or both of the user's hands may be moved from a hand-held tool to perform the user input gesture.

In some implementations, one or more of the handheld tools within the surgical field 206 may include a user input device, such as a touch-sensitive pad. For example, an exterior surface of the surgical instrument 114 may include a touchpad in the area of the instrument that is ordinarily grasped by the user. A touch-sensitive pad can be disposed on the surgical instrument 114, illumination device 244, infusion device 246, aspiration device 250, laser device 248, the surgical microscope 120, the console 150, and/or other component of the system 100.

The computing device 210 may process signals representative of the user's hand or finger movements on the touchpad to determine user input gestures to make GUI selections. In some implementations, the input device 218 may be a tablet device. For example, the tablet device can be positioned remote from the microscope 120 and/or the console 150. The tablet device can be in wired or wireless communication with the microscope 120 and/or the console 150, and communicatively coupled to the surgical instrument 144, e.g., via the console 150.

In some instances, the input device 218 may be a control device that uses a gaze as an input and may be configured to detect and track the eyes of the user 202 to determine user input. In some instances, the input device 218 may be a voice recognition device configured to receive user input via the voice commands issued by the user 202. The computing device 210 may process signals representative of the user's voice or eye movements to make GUI selections.

In some implementations, the user input device 218 includes an instrument tracking system. The instrument tracking system may include an imaging device that tracks the position of the surgical instrument 114 and/or other tool within the surgical field 206. For example, in some instances, the imaging device may identify movement of the distal tip of the surgical instrument 114, including when distal tip is in contact with the anatomy and when the distal tip is spaced apart from anatomy. The imaging data acquired by the imaging device may be processed by the computing device 210 to recognize various user inputs. For example, the computing device 210 may distinguish between movements made while the distal tip is spaced apart from anatomy and movements made while the distal tip is proximate to or in contact with anatomy. For example, in some implementations, the computing device may interpret movements made while the distal tip is spaced apart from anatomy as user inputs to make GUI selections.

Generally, the surgical microscope 120 may be any surgical microscope configured for use during an ophthalmic procedure. The optical train housing 132 of microscope 120 is shown and may include lenses 242a, 242b, such as focusing lens(es), zoom lens(es), and an objective lens 238. The user 202 may adjust the magnification and/or field of view by changing the relative positioning of the zoom lens(es). It is understood that various mirrors, filters, gratings, and/or other optical components, such as a beam splitter 236 and beam couplers 234a, 234b, may be included in the housing 132.

The ophthalmic surgical system 200 may include an imaging device 232. The imaging device 232 may be a digital imaging device. For example, a camera or video camera may be configured to acquire a series of still images or frames of the surgical field 206 that together form a live, real-time view thereof. In that regard, the imaging device 232 may include an image sensor, such as a charge coupled device (CCD) image sensor, complementary metal-oxide-semiconductor (CMOS) sensor, and/or other image sensors. The imaging device 232 may be configured to receive light reflected from the surgical field 206.

The beam splitter 236 may be configured to guide a portion of the reflected light through a lens 231 to the imaging device 232 while allowing another portion of the reflected light to pass through to the eyepiece 122. The beam splitter 236 may include, for example, a glass prism, a metallic-coated mirror, a dichroic mirror, dichroic mirrored prism, a notch filter, a hot mirror, a cold mirror, and/or other optical devices. The portion of the reflected light directed towards the imaging device 232 may be split at any suitable point along the optical path, such as within or outside the surgical microscope 120. For example, the beam splitter 236 may be positioned between the eyepiece 122 and the objective lens 238, or between the lens 242b and the objective lens 238. The imaging device 232 may also include processing components, memory components, and/or other electrical components to interpret the light received at the image sensor and generate image data for use by the computing device 210 communicatively coupled thereto. The imaging device 232 may transmit the image data to the computing device 210.

The ophthalmic surgical system 200 can include display devices 222a, 222b operable to output a graphical overlay into the optical path of the surgical microscope 120. With a stereo microscope, as in the illustrated implementation of FIG. 2, the two display devices 222a, 222b correspond to the different optical paths for each eye of the user 202. In other implementations, a single display device may output a graphical overlay into both optical paths.

The display devices 222a, 222b may be any display device, including, for example, a projection device, such as a digital light processing (DLP) device, a liquid crystal display (LCD) device, a light emitting diode (LED) device, a liquid crystal on silicon (LCoS) device, other devices, and/or combinations thereof. The display devices 222a, 222b may be in optical communication with the surgical microscope 120 such that the observer 202 may view the graphical overlay while simultaneously observing the surgical field 206 using the surgical microscope 120. Light from the display devices 222a, 222b passes through lenses 224a, 224b, respectively, to the beam couplers 234a, 234b. The beam couplers 234a, 234b are configured to combine the light from the display devices 222a, 222b, respectively, with the light reflected from the surgical field 206. The combined light is received at the eyepiece 122. In some implementations, the beam couplers 234a, 234b may include, for example, a glass prism, a metallic-coated mirror, a dichroic mirror, dichroic mirrored prism, a notch filter, a hot mirror, and/or a cold mirror. The light from the display devices 222a, 222b may be combined with the reflected light at any point along the optical path, such as, for example, within or outside the surgical microscope 120. In some instances, the beam couplers 234a, 234b may be positioned between the eyepiece 122 and the objective lens 238, as shown. In other instances, the beam couplers 234a, 234b may be positioned elsewhere in the microscope 120.

The imaging device 232 and the display devices 222a, 222b may be fixedly or removably coupled to the surgical microscope 120. For example, fixedly-coupled devices may be integrated with or integrally disposed on/within the surgical microscope 120. For example, removably-coupled devices may be included in an add-on module that may be selectively added or removed from the surgical microscope 120. The surgical microscope 120 may include various components (e.g., wires, contacts, interfaces, etc.) for facilitating electrical, optical, and/or data communication between the computing device 210, the imaging device 232, the display devices 222a, 222b, and/or the input device 218.

Figure 3:
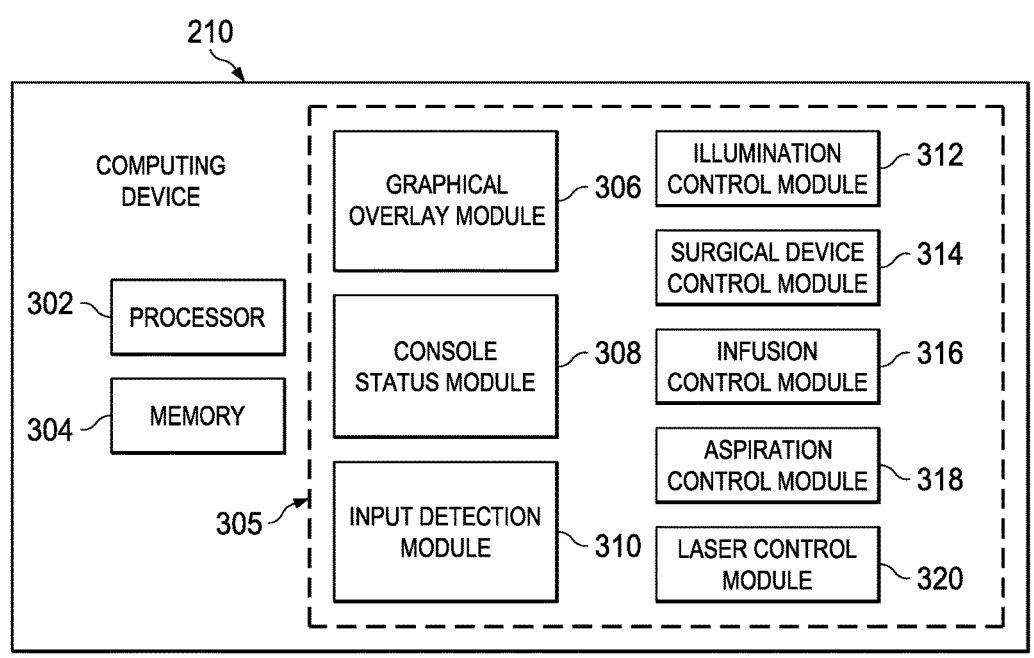
FIG. 3 is a block diagram of the computing device of FIG. 2.

FIG. 3 is a block diagram of the computing device 210 according to some implementations. The computing device 210 includes a processing circuit, such as one or more processors 302 in communication with a memory 304. The computing device 210 also includes one or more programmable processor units 305 running programmable code instructions. In this example, the programmable processor units 305 include a graphical overlay module 306, a console status module 308, an input detection module 310, an illumination control module 312, a surgical device control module 314, an infusion control module 316, and aspiration control module 318, and a laser control module 320. The processor(s) 302 may execute computer instructions stored on the memory 304 to allow a user to select console settings via a GUI displayed in the microscope view. The memory 304, which is typically a semiconductor memory, such as, for example, random access memory (RAM), ferroelectric random access memory (FRAM), or flash memory, interfaces with the processor(s) 302. As such, the processor(s) 302 may write to and read from the memory 304, and perform other common functions associated with managing semiconductor memory 304. Processing circuit(s) of the computing device 210 may be integrated circuits with power, input, and output pins capable of performing logic functions. In various implementations, the processor 302 of the computing device 210 is a targeted device controller, or a microprocessor configured to control more than one component of the surgical system 100 or 200, and/or a combination thereof.

The graphical overlay module 306 includes computer-executable instructions for generating display data associated with a graphical overlay. For example, the graphical overlay may include a GUI for selecting and/or modifying one or more console settings. For example, with the graphical overlay module 306, a user may select or modify the operating frequency or cut speed of the surgical instrument 114, the wavelength and/or intensity of the illumination device 244, the desired intraocular pressure associated with the infusion device 246, the wavelength, spot size, power, and/or pulse duration of the laser device 248, an aspiration level associated with the aspiration device 250, and/or other parameters of the ophthalmic surgical system. While examples of the console settings are provided, particularly as they apply to the different devices, the scope of the disclosure is not so limited. Rather, the examples provided are merely illustrative. Other console settings related to one or more of the devices or associated with other aspects of a surgical system, such as, for example, the ophthalmic surgical system 100 shown in FIG. 1, are also within the scope of the disclosure.

Figure 4:
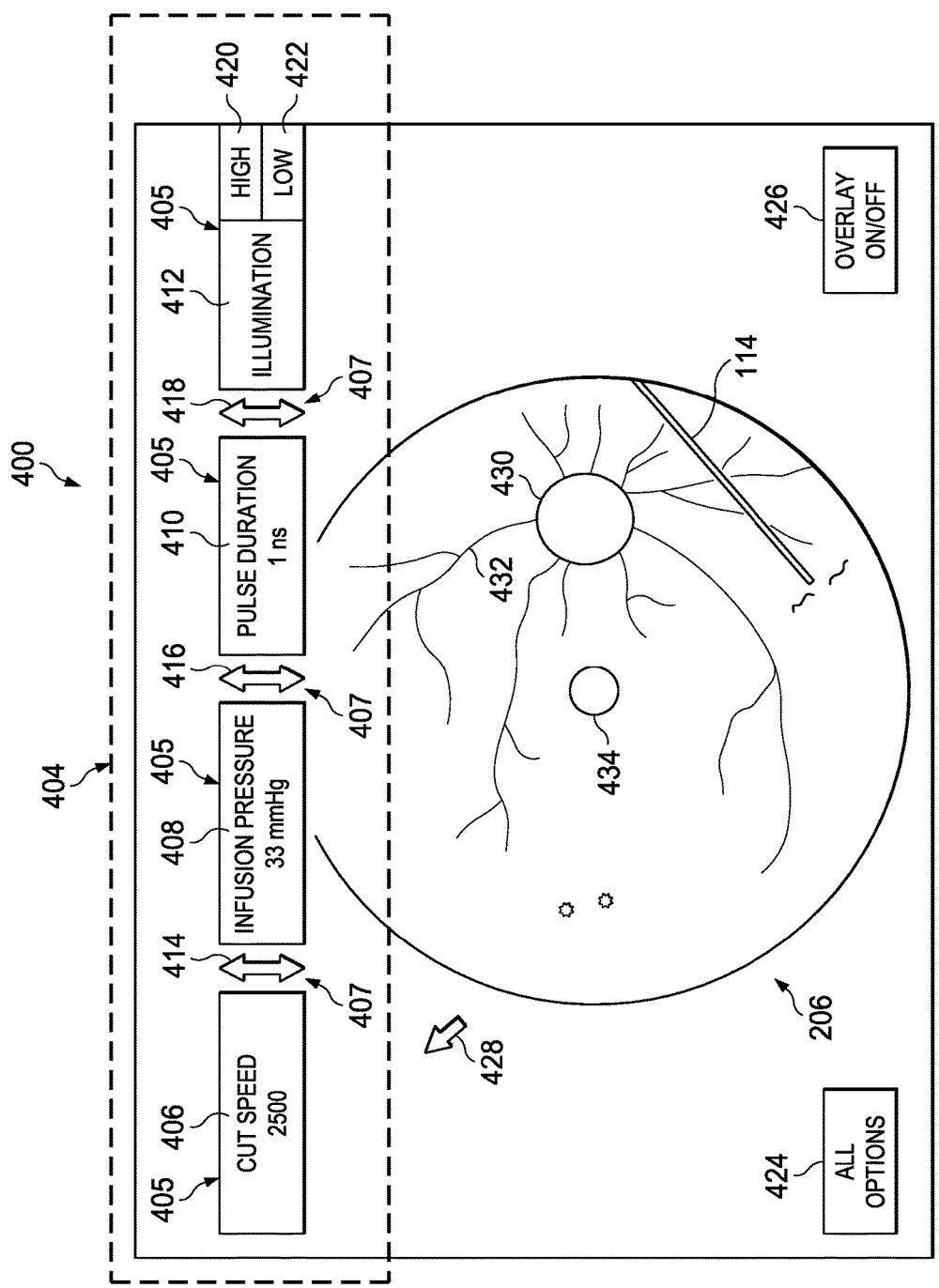
FIG. 4 shows an example graphical overlay on the field of view of the surgical microscope of FIG. 2.

The computing device 210 may transmit the display data to the display devices 222a, 222b (shown in FIG. 2), which output the GUI into the field of view of the surgical microscope 120. An exemplary implementation of a GUI generated by the graphical overlay module 306 is illustrated in FIG. 4. As shown in FIG. 4 and discussed in more detail below, the graphical overlay may be positioned over a portion of the user's field of view. The graphic overlay module 306 and/or the display devices 222a, 222b may be configured to provide the graphical overlay with varying parameters, such as, for example, size, shape, position, transparency.

The console status module 308 includes computer-executable instructions for determining the operating status of the console and/or the tools in communication therewith. For example, the computing device 210 may receive signals indicating the current operating status (e.g., actual cut speed, actual infusion pressure, etc.) from the surgical instrument 114, the illumination device 244, the infusion device 246, the laser device 248, and/or the aspiration device 250. Graphical representation(s) of the received status signals may be included in the graphical overlay generated by the graphical overlay module 306. In some instances, controls signals generated and transmitted to the surgical tools by the computing device 210 may be considered the received status signals.

The input detection module 310 includes computer-executable instructions for determining user input(s) that are used to select and/or modify one or more console settings via the GUI viewable using the microscope 120. The input detection module 310 may be configured to recognize, for example, footswitch button selection, instrument button selection, hand or finger gestures, instrument movement, and/or inputs from any other input device, such as the input device 218 (shown in FIG. 2). In that regard, the input detection module 310 processes signals received from the input device 218 and/or the imaging device 232. For example, in implementations in which the location of the surgical instrument 114 is monitored, the input detection module 310 may identify user inputs from imaging data obtained by the imaging device 232. For example, the input detection module 310 may be operable determine a user input based on a position of a portion of an instrument within the eye. For example, changes in positioning of a portion of an instrument relative to an ocular tissue may correspond to different user inputs. In other implementation, movement of a portion of an instrument relative to an ocular tissue, such as, for example, when the instrument is pulled away from tissue, may be interpreted as a user input. For example, in some instances, the input detection module 310 may then interpret movement of the instrument 114 as a pointer selecting one or more GUI options displayed in the field of view of the microscope 120. In implementations in which the user's finger and/or hand movement is tracked, the input detection module 310 may determine from imaging data obtained by the imaging device 232 when the user's gesture corresponds to a GUI selection.

The illumination control module 312, the surgical device control module 314, the infusion control module 316, the aspiration control module 318, and/or the laser control module 320 include computer-executable instructions for generating control signals for the illumination device 244, surgical instrument 114, infusion device 246, aspiration device 250, and the laser device 248, respectively. The control signals may be representative of the operating parameter(s) for the respective surgical tool. For example, the control signals may cause activation or deactivation of a surgical tool, functioning of the surgical tool at a set value, an increase, decrease, other change in the operation of the surgical tool, or may otherwise control surgical tool operation. The computing device 210 may generate and transmit the control signals in response to user inputs determined by the input detection module 310 and/or the current status of the surgical tool(s) determined by the console status module 308.

FIG. 4 illustrates am example field of view 400 that may be seen through a surgical microscope (e.g., the surgical microscope 120 of FIGS. 1 and 2). A user may observe the surgical field 206 and the graphical overlay 404 through the eyepiece of the surgical microscope 120. The field of view 400 may be described as the heads up display of the surgical microscope 120. In the example illustrated, the surgical field 206 includes anatomy within the eye. Particularly, in this example the surgical field 206 includes retina 430, blood vessel 432, and macula 434. A distal end of the surgical instrument 114 is also visible in the surgical field 206. While only one surgical instrument 114 is illustrated in FIG. 4, it is understood that any number of instruments (e.g., including the illumination device 244, the infusion device 246, the laser device 248, the aspiration device 250, and/or other suitable instrument) may be simultaneously positioned within the surgical field. The parameter(s) associated with the one or more instruments can be viewed and adjusted using the graphical overlay 404.

The graphical overlay 404 includes a cursor 428, parameter fields 405 that provide parameter data, and adjustment fields 407 selectable to change the parameters. In this implementation, the parameter fields 405 include a cut speed set point 406, an infusion pressure set point 408, a laser pulse duration set point 410, and an illumination level set point 412. An adjustment field 407 is associated with each parameter field 405. Adjustment field 414 is associated with the cut speed set point 406, adjustment field 416 is associated with the infusion pressure set point 408, adjustment field 418 is associated with a laser pulse duration set point 410, and adjustment fields 420, 422 are associated with an illumination level set point 412. Adjustment fields 414, 416, and 418 allow the user to increase or decrease the cut speed set point, infusion pressure set point, and/or the laser pulse duration set point, respectively. Adjustment fields 420, 422 allow a user to select a high or low illumination level set point.

It is understood that the parameter fields 405 and/or the adjustment fields 407 are not limited to the sizes and shapes shown in FIG. 4. Rather, the parameter fields 405 and/or the adjustment fields 407 may be any graphical representation of any size or shape to allow the user to view, select, and/or modify a console parameter. The parameter fields 405 and/or the adjustment fields 407 can be variously positioned within the field of view 400. For example, in some instances, the parameter fields 405 and/or the adjustment fields 407 may be positioned surrounding the view of the surgical field 206, such as circumferentially around the view of the surgical field 206. In some implementations, one or more the parameter fields 405 and/or one or more the adjustment fields 407 may be positioned on a left side, a right side, above, and/or below the view of the surgical field 206 as those positions are understood with respect to FIG. 4. For example, in some instances, one or more parameter fields 405 and adjustment fields 407 can be positioned on the right side and the left side of the view of the surgical field 206. In some instances, the parameter fields 405 and adjustment fields 407 may be spaced apart from the view of the surgical field 206. In this regard, the parameter fields 405 and adjustment fields 407 may be positioned so as not to overlap all or a portion of the view of the surgical field 206. In some instances, the graphical overlay omits the adjustment fields 407 and integrates their functionality in the parameter fields 405. For example, the user 202 may adjust the parameter by providing a user input on the parameter field 405.

The cursor 428 may be controlled by the user to select one of more options of the graphical overlay 404. The parameter fields 405 may provide an alphanumeric representation, symbolic, and/or graphical representation identifying the parameter, a set point, and/or a current status of the parameter. For example, the parameter field 405 may include text, an abbreviation of the text, a symbol, a graphic, a logo, a numerical value, a unit of measurement, and/or other content to allow the user 202, for example, to understand the nature of the parameter field and a current setting thereof; and to view and/or adjust one or more parameters. Four exemplary console parameters are illustrated in FIG. 4. It is understood that one, two, three, four, or more parameter fields 405 may be included in the graphical overlay 404 in various implementations. Further, the number and nature of the parameter fields displayed may vary depending upon various factors, such as, for example, the nature of the surgical procedure being performed, the stage or phase of the surgical procedure, the number of instruments being utilized, or the personal preferences of the user. The console parameters listed in the parameter fields 405 may include a set point for cut speed, operating frequency, infusion pressure, alternative infusion pressure, illumination level, illumination wavelength, vacuum aspiration level, laser power, laser pulse duration, laser wavelength, and/or other parameters. The console parameters described in the parameter fields 405 may also include the current/actual status of one or more console parameters, including cut speed, operating frequency, infusion pressure, illumination level, illumination wavelength, vacuum aspiration level, laser power, laser pulse duration, laser wavelength, laser energy diathermy power, diathermy energy and/or other parameters.

Respective adjustment fields 407 are displayed adjacent to the parameter fields 405. The user may move the cursor 428 over an adjustment field 407 and make a selection to change a console parameter set point. For example, to increase or decrease the cut speed set point 406, the user may select the up arrow or down arrow, respectively, in the adjustment field 414 using the cursor 428. In that regard, some adjustments fields may allow for scrolling between set point values (e.g., adjustment fields 414, 416, 418, etc.) while other adjustment fields allow for selection among a list of set point options (e.g., adjustment fields 420, 422). For example, the user may select between the high option 420 and the low option 422 for the illumination level set point 412. The graphical overlay 404 may also include a parameter field and/or an adjustment field to activate injection of gas, liquid, air, silicone oil, and/or other material into the eye.

In some implementations, the graphical overlay 404 is always activated while the console 150 and/or surgical microscope 120 are operable. In some implementations, the overlay 404 may be selectively activated, such as by a user. For example, in some instances, the field of view 400 may not include the overlay 404 until the overlay is manually or automatically activated. For example, in some implementations, the field of view 400 may include an activation field 426 to manually activate or deactivate the graphical overlay 404 in response to a user selection of that field. In other instances, the graphical overlay 404 may be automatically activated based on a user input and/or based on a setting or an occurrence of an event. An occurrence of an event that triggers the activation or deactivation of the graphical overlay 404 may be detected by the ophthalmic surgical system 100, e.g., the computing device 210.

In some implementations, the graphical overlay 404 may be provided when the user initiates movement of the cursor 428. In some implementations, the graphical overlay 404 may be automatically activated when the computing device determines, based on a user input signal, that the user desires to set or adjust a console parameter. For example, in an implementation in which the surgical instrument 114 is tracked, the graphical overlay 404 may be activated when the surgical instrument 114 is moved away from anatomy within the eye. In some instances, the graphical overlay 404 may be deactivated when the surgical instrument 114 is moved towards the anatomy. In some implementations, a button or control device disposed on the user input device (e.g., the footswitch, the surgical instrument, etc.) may be selected to activate or deactivate the graphical overlay 404. In some implementations, the graphical overlay 404 is automatically deactivated or times out after a period of time.

The implementation shown in FIG. 4 may provide the option of selecting or adjusting a small number of console settings from among many settings. In that regard, the graphical overlay 404 may be considered a quick or abbreviated options menu that provides access to a specific group of console settings, such as the most-frequently used console settings or the graphic overlay 404 may represent an example user-selected preference of console settings. In some implementations, an all options field 424 is included in the graphical overlay 404. Selection of the all options field 424 may cause a full menu of console setting to be displayed over the surgical field 206. In that regard, the full menu of console settings may be similar to the GUI of the console display 106 (FIG. 1). Using the full menu, the user may be able to change any desired console setting from the heads up display.

Various visual or graphical settings associated with the graphical overlay 404 may be adjustable by a user. For example, the graphical overlay may have an associated position, transparency, size, color, contrast, and/or other suitable graphical parameter. For example, the parameter fields and/or adjustment fields may be positioned at the top, at the bottom, and/or along the side(s) of the field of view 400. As another example, the transparency of the graphical overlay 404 may be set such that the surgical field 206 is still viewable through parameter fields and/or adjustment fields.

Figure 5:
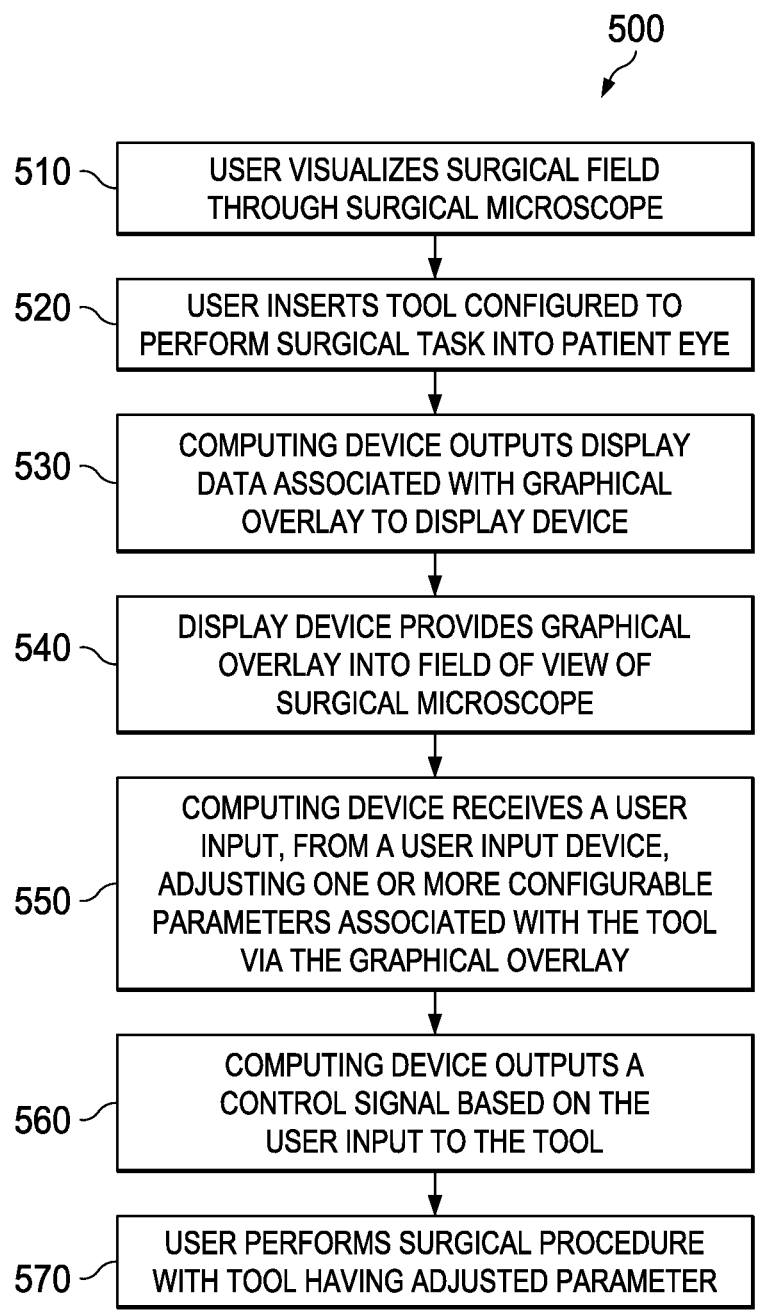
FIG. 5 is a flow diagram of an example method of operating an ophthalmic surgical system.

FIG. 5 illustrates a flowchart of an example method 500 of operating an ophthalmic surgical system. As illustrated, the method 500 includes a number of enumerated steps, but implementations of the method 500 may include additional steps before, after, and in between the enumerated steps. In some implementations, one or more of the enumerated steps may be omitted or performed in a different order.

At step 510, the method 500 includes the user visualizing the surgical field, such as a patient's eye, through a surgical microscope. In that regard, the user may view the surgical field using the microscope optics. At step 520, the method 500 includes the user inserting a surgical tool into the patient's eye. The surgical tool, such as a cutting probe or vitrectomy probe, may be configured to perform a surgical task. The surgical tool may be in communication with a surgical console. In some implementations, multiple surgical tools may be inserted into the patient's eye at step 520, such as an infusion cannula, an illumination device, and a cutting probe, among others.

At step 530, the method 500 includes a computing device outputting display data associated with a graphical overlay to a display device. The computing device may be in communication with the surgical microscope and/or the surgical console. The display device may be in optical communication with the surgical microscope such that the graphical overlay may be provided into the visual path or field of view of the surgical microscope. A step 540, the method 500 includes the display device providing the graphical overlay into the field of view of the surgical microscope. For example, the user may simultaneously view the surgical field and the graphical overlay through the surgical microscope. The graphical overlay may include one or more configurable parameters associated with the tool(s) inserted into the eye in step 520. In some implementations, the graphical overlay may include a graphical representation of a set point and/or a current status of the parameters. In some implementations, the graphical overlay includes an adjustment feature (e.g., a list of options, a scroll bar or arrow, etc.) to modify the one or more configurable parameters. In some implementations, the method 500 includes receiving a user input to show or hide the graphical overlay.

At step 550, the method 500 includes the computing device receiving a user input adjusting one or more of the configurable parameters of the tool(s). For example, the user input may increase, decrease, and/or otherwise modify operation of the surgical tool(s) inserted into the eye. The user input may be received from a user input device. In some implementations, the user input may be representative of a user gesture (e.g., with a hand or finger), a tool motion, a selection of a footswitch button, and/or a selection of a tool button. Other user inputs may also be used.

At step 560, the method 500 includes the computing device outputting a control signal based on the user input to the surgical tool(s). The computing device may generate the control signal to implement the modified console parameter selected by the user in step 540. For example, the control signal may increase, decrease, and/or otherwise modify operation of the surgical tool. At step 570, the method 500 includes the user performing the surgical procedure using the tool with the adjusted parameter. For example, the user may perform a vitrectomy procedure using a vitrectomy probe with a modified operating frequency.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ophthalmic surgical system, comprising:
   a surgical microscope operable to provide a field of view of a surgical site to a user;
   a display device in communication with the surgical microscope, the display device operable to output a graphical overlay into the field of view of the surgical microscope;

a surgical tool configured to be inserted into a patient and operable to perform a surgical task at the surgical site while the user visualizes the field of view using the surgical microscope, wherein the graphical overlay displays one or more configurable parameters that modify operation of the surgical tool;

an input device operable to receive user input from the user to adjust the one or more configurable parameters associated with the surgical tool, the user input entered using the graphical overlay while the user visualizes the field of view using the surgical microscope; and a computing device operable to:
  generate a control signal to adjust the one or more configurable parameters that modify the operation of the surgical tool in the response to the user input entered using the graphical overlay; and
  output the control signal to the surgical tool to control the surgical tool to perform the surgical task at the surgical site according to the user input entered using the graphical overlay.

2. The system of claim 1, wherein the display device is operable to simultaneously display the graphical overlay and the field of view of the surgical site.

3. The system of claim 1, wherein the graphical overlay includes a graphical representation of at least one of a set point or a current status of the one or more configurable parameters.

4. The system of claim 3, wherein the graphical overlay includes an adjustment field operable to modify the one or more configurable parameters.

5. The system of claim 1, wherein the tool includes at least one of a cutting probe, a vitrectomy probe, a phacoemulsification probe, a laser probe, an ablation probe, a diathermy probe, a vacuum probe, a flushing probe, scissors, forceps, an infusion device, an aspiration device, an illumination device, a laser, or an endoscopic visualization probe.

6. The system of claim 1, wherein the one or more parameters includes at least one of a cut speed, an operating frequency, an infusion pressure, an alternative infusion pressure, an illumination level, an illumination wavelength, a vacuum aspiration level, a laser power, a laser pulse duration, a laser wavelength, laser energy diathermy power, or diathermy energy.

7. The system of claim 1, wherein the input device includes at least one of an imaging device, a footswitch, a touch-sensitive pad, a tablet device, a gesture control device, a voice recognition device, or a gaze control device.

8. The system of claim 1, further comprising a surgical console in communication with at least one of the surgical microscope, the display device, the tool, or the input device, the surgical console being configured to receive and respond to control signals indicative of adjustment of the one or more configurable parameters.

9. The system of claim 1, further comprising a second tool operable to perform a surgical task associated with the surgical site while the user visualizes the field of view using the surgical microscope, wherein the graphical overlay displays one or more configurable parameters associated with the second tool.

10. An ophthalmic surgical system, comprising:
  a computing device operable to:
    output display data representative of a graphical overlay including one or more configurable parameters that modify operation of a surgical tool, the surgical tool configured to be inserted into a patient and operable to perform a surgical task at a surgical site during an ophthalmic surgical procedure;
    receive a user input entered using the graphical overlay, the user input adjusting the one or more configurable parameters associated with the surgical tool;
    generate a control signal to adjust the one or more configurable parameters that modify the operation of the surgical tool in the response to the user input entered using the graphical overlay; and
    output, to the surgical tool, a control signal to control the surgical tool to perform the surgical task on at surgical site according to the user input entered using the graphical overlay, the control signal adjusting the one or more configurable parameters associated with the surgical tool; and
  a display device operable to provide the graphical overlay into a field of view of a surgical microscope.

11. The system of claim 10, wherein the display device is operable to simultaneously display the graphical overlay and the field of view of the surgical site.

12. The system of claim 10, wherein the display data includes a graphical representation of at least one of a set point or a current status of the one or more configurable parameters.

13. The system of claim 10, wherein the display data includes a graphical representation of an adjustment feature to modify the one or more configurable parameters.

14. The system of claim 10, wherein the user input is representative of at least one of a user gesture, a tool motion, a selection of a footswitch button, or a selection of a tool button.

15. The system of claim 10, wherein computing device is further operable to:
  receive, from the input device, a user input to selectively show or hide the graphical overlay.

16. A method of operating an ophthalmic surgical system, the method comprising:
  outputting, from a computing device to a display device, display data representative of a graphical overlay including one or more configurable parameters that modify operation of a surgical tool, the surgical tool configured to be inserted into a patient and operable to perform a surgical task during an ophthalmic surgical procedure;
  displaying the graphical overlay within a field of view of a surgical microscope operable by a user to visualize a patient eye;
  receiving a user input entered using the graphical overlay, the user input adjusting the one or more configurable parameters associated with the surgical tool;
  generating a control signal to adjust the one or more configurable parameters that modify the operation of the surgical tool in the response to the user input entered using the graphical overlay; and
  outputting, to the surgical tool, a control signal to control the surgical tool to perform the surgical task according to the user input entered using the graphical overlay, the control signal adjusting the one or more configurable parameters associated with the surgical tool.

17. The method of claim 16, wherein the display data includes a graphical representation of at least one of a set point or a current status of the one or more configurable parameters.

18. The method of claim 16, wherein the display data includes a graphical representation of an adjustment feature to modify the one or more configurable parameters.

19. The method of claim 16, wherein the user input is representative of at least one of a user gesture, a tool motion, a selection of a footswitch button, or a selection of a tool button.

20. The method of claim 16, further comprising:
  receiving, from the input device, a user input to selectively show or hide the graphical overlay.

\* \* \* \* \*